United States Patent
Rosa et al.

(10) Patent No.: US 10,501,447 B2
(45) Date of Patent: Dec. 10, 2019

(54) IMIDAZOLECARBOXAMIDES AND THEIR USE AS FAAH INHIBITORS

(71) Applicant: BIAL-PORTELA & Ca, S.A., S. Mamede do Coronado (PT)

(72) Inventors: Carla Patrícia Da Costa Pereira Rosa, S. Mamede do Coronado (PT); Rita Gusmão De Noronha, S. Mamede do Coronado (PT); Laszlo Erno Kiss, S. Mamede do Coronado (PT)

(73) Assignee: BIAL-PORTELA & C$^a$, S.A., S. Mamede do Coronado (PT)

( * ) Notice: Subject to any disclaimer, the term of this patent is extended or adjusted under 35 U.S.C. 154(b) by 22 days.

(21) Appl. No.: 14/906,822

(22) PCT Filed: Jul. 24, 2014

(86) PCT No.: PCT/PT2014/000049
§ 371 (c)(1),
(2) Date: Jan. 21, 2016

(87) PCT Pub. No.: WO2015/012708
PCT Pub. Date: Jan. 29, 2015

(65) Prior Publication Data
US 2016/0176854 A1  Jun. 23, 2016

(30) Foreign Application Priority Data

Jul. 24, 2013 (GB) .................................. 1313202.2
Jul. 24, 2013 (GB) .................................. 1313203.0
Jul. 24, 2013 (GB) .................................. 1313204.8

(51) Int. Cl.
*A61K 31/4178* (2006.01)
*C07D 419/04* (2006.01)
(Continued)

(52) U.S. Cl.
CPC ........ *C07D 405/12* (2013.01); *A61K 31/4178* (2013.01); *A61K 31/454* (2013.01);
(Continued)

(58) Field of Classification Search
CPC .............. A61K 31/4178; C07D 405/12; C07D 419/04; C07D 419/10
See application file for complete search history.

(56) References Cited

U.S. PATENT DOCUMENTS 4,051,252 A   9/1977  Mayer et al.
4,331,678 A   5/1982  De'Ath et al.
(Continued)

FOREIGN PATENT DOCUMENTS

WO   2005073199 A1   8/2005
WO   2008129129 A1   10/2008
(Continued)

OTHER PUBLICATIONS

Liu et al. Journal of Huazhong University of Science and Technology [Medical Sciences], Apr. 2009, vol. 29, Issue 2, pp. 182-186.*
Altinsoy et al. A Cannabinoid Ligand, Anandamide, Exacerbates Endotoxin-Induced Uveitis in Rabbits. Association for Ocular Pharmacology and Therapeutics, Aug. 2011; 27(6):545-52.*
Gerald Litwack. Vitamins and Hormones: Anandamide an Endogenous Cannabinoid. London: Elsevier Inc., 2009. Pages 498-499.*
Francesco Boscia, MD. ("When to Treat and Not to Treat Patients With Central Serous Retinopathy" Retina Today | Apr. 2010 , pp. 42-44), (Year: 2010).*
Mikawa et al. ("Ocular activity of topically administered anandamide in the rabbit." Japanese Journal of Ophthalmology; vol. 41, Issue 4, Jul.-Aug. 1997, pp. 217-220. Abstract only.). (Year: 1997).*
Cheng et al., "Specific CB2 Receptor Agonist Suppresses the Murine Model of Experimental Autoimmune Uveitis," ARVO Annual Meeting Abstract, Investigative Ophthalmology & Visual Science 45, 552, 2004.
(Continued)

*Primary Examiner* — Rachael E Bredefeld
*Assistant Examiner* — Chris E Simmons
(74) *Attorney, Agent, or Firm* — Banner & Witcoff, Ltd.

(57) ABSTRACT

A compound having a structure selected from the following:

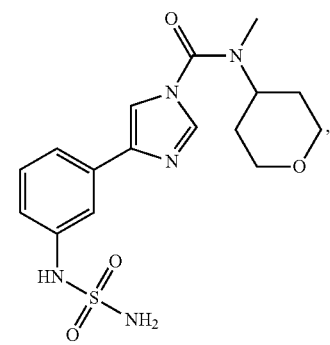

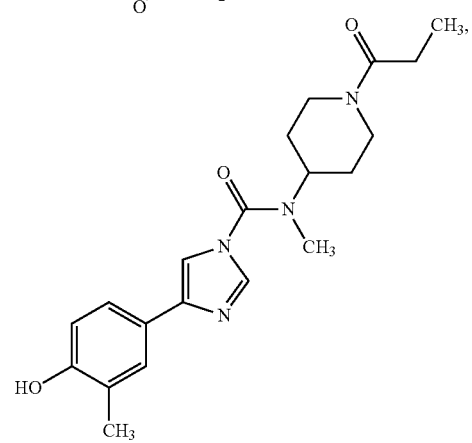

(Continued)

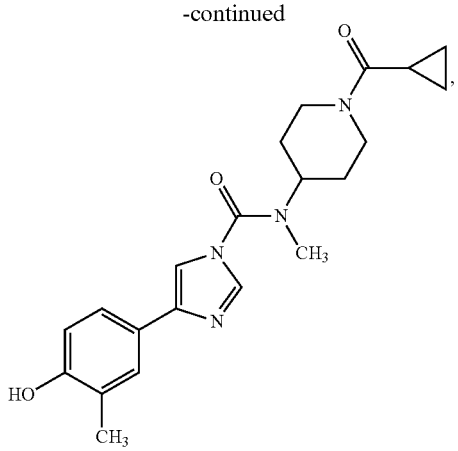

or a pharmaceutically acceptable salt thereof. The compound may be used as an inhibitor of fatty acid amide hydrolase.

15 Claims, No Drawings

(51) Int. Cl.
  C07D 419/10 (2006.01)
  C07D 405/12 (2006.01)
  C07D 401/12 (2006.01)
  C07D 235/24 (2006.01)
  A61K 31/454 (2006.01)
  A61K 45/06 (2006.01)

(52) U.S. Cl.
  CPC ............ *A61K 45/06* (2013.01); *C07D 235/24* (2013.01); *C07D 401/12* (2013.01)

(56) References Cited

U.S. PATENT DOCUMENTS

| | | | |
|---|---|---|---|
| 4,973,588 A | 11/1990 | Kihara et al. | |
| 5,578,627 A | 11/1996 | Takeda et al. | |
| 8,324,241 B2 | 12/2012 | Huang et al. | |
| 9,353,082 B2 | 5/2016 | Kiss et al. | |
| 9,549,915 B2 | 1/2017 | Rosa et al. | |
| 10,023,541 B2 | 7/2018 | Rosa et al. | |
| 2005/0197348 A1 | 9/2005 | Zoller et al. | |
| 2009/0215824 A1 | 8/2009 | Zoller et al. | |
| 2012/0065191 A1 | 3/2012 | Kiss et al. | |

FOREIGN PATENT DOCUMENTS

| | | |
|---|---|---|
| WO | 2010074588 A2 | 7/2010 |
| WO | 20120015324 A1 | 2/2012 |
| WO | 2012038904 A1 | 3/2012 |
| WO | 2014017936 A2 | 1/2014 |

OTHER PUBLICATIONS

Deng, "Recent advances in the discovery and evaluation of fatty acid amide hydrolase inhibitors," Expert Op. Drug Disc. [Early Online] 2010, 1-33.

Pacher et al., "The Endocannabinoid System as an Emerging Target of Pharmacotherapy," Pharmacol. Rev. 58, 389-462, 2006.

Schlosburg et al., "Targeting Fatty Acid Amide Hydrolase (FAAH) to Treat Pain and Inflammation," The AAPS Journal, published online Jan. 29, 2009, pp. 1-6.

International Search Report dated Sep. 25, 2014, for PCT/PT2014/00049.

Da Silva et al., "Zinc-promoted, iridium catalyzed reductive alkylation of primary amines with aliphatic ketones in aqueous medium," Tetrahedron Letters 51, 689-91, 2010.

Dorwald, "Side Reactions in Organic Synthesis," 2005, Wiley: VCH Weinheim Preface, pp. 1-15 & Chapter 8, pp. 279-308.

International Search Report and Written Opinion for PCT/PT2013/000050 dated Jan. 30, 2014.

International Search Report for PCT/PT2013/000048 dated Jul. 25, 2014.

Kasnanen et al., "3-Heterocycle-Phenyl N-Alkylcarbamates as Faah Inhibitors: Design, Synthesis and 3D-QSAR Studies," ChemMedChem 5, 213-31, 2010.

Nucci et al., "Involvement of the Endocannabinoid System in Retinal Damage after High Intraocular Pressure-Induced Ischemia in Rats," Investigative Ophthalmology & Visual Science 48, 2997-3004, 2007.

Tomida et al., "Cannabinoids and glaucoma," Br. J. Ophthalmol. 88, 708-13, 2004.

\* cited by examiner

IMIDAZOLECARBOXAMIDES AND THEIR USE AS FAAH INHIBITORS

This application is the U.S. national stage of PCT/PT2014/000049, filed on Jul. 24, 2014, which claims priority to GB 1313202.2 filed on Jul. 24, 2013, GB 1313203.0 filed on Jul. 24, 2013, and GB 1313204.8 filed on Jul. 24, 2013.

FIELD OF THE INVENTION

The present invention relates to a compound and its use, and in particular to a compound and its therapeutic use in the treatment or prevention of conditions having an association with substrates, such as the neurotransmitter anandamide, which are broken down by the fatty acid amide hydrolase (FAAH) enzyme.

BACKGROUND TO THE INVENTION

FAAH enzyme breaks down fatty acid amides such as anandamide (N-arachidonoylethanolamine), N-oleoylethanolamine (OEA), N-palmitoylethanolamine (PEA) and oleamide. Anandamide, also known as N-arachidonoylethanolamine or AEA, is an endogenous cannabinoid neurotransmitter found in animal and human organs, especially in the brain. It has also been found that anandamide binds to the vanilloid receptor. Anandamide is degraded by the fatty acid amide hydrolase (FAAH) enzyme to ethanolamine and arachidonic acid. Accordingly, inhibitors of FAAH lead to elevated anandamide levels.

Anandamide is a neurotransmitter in the endocannabinoid system and stimulates the cannabinoid receptors. Cannabinoid receptors, such as CB1 and CB2, are G protein-coupled receptors. CB1 is found mainly in the central nervous system whereas CB2 is found mainly in peripheral tissue. The endocannabinoid system has been implicated in a growing number of physiological functions, both in the central and peripheral nervous systems and in peripheral organs. Modulation of the activity of the endocannabinoid system has been shown to have a potentially therapeutic effect on a wide range of disparate diseases and pathological conditions. Therefore, the endocannabinoid system, and the FAAH enzyme in particular, has become a therapeutic target for developing potential treatments for many diseases. The endocannabinoid system has been implicated in appetite regulation, obesity, metabolic disorders, cachexia, anorexia, pain, inflammation, neurotoxicity, neurotrauma, stroke, multiple sclerosis, spinal cord injury, Parkinson's disease, levodopa-induced dyskinesia, Huntington's disease, Gilles de la Tourette's syndrome, tardive dyskinesia, dystonia, amyotrophic lateral sclerosis, Alzheimer's disease, epilepsy, schizophrenia, anxiety, depression, insomnia, nausea, emesis, alcohol disorders, drug addictions such as opiates, nicotine, cocaine, alcohol and psychostimulants, hypertension, circulatory shock, myocardial reperfusion injury, atherosclerosis, asthma, glaucoma, retinopathy, cancer, inflammatory bowel disease, acute and chronic liver disease such as hepatitis and liver cirrhosis, arthritis and osteoporosis. The endocannabinoid system and the conditions with which it is associated is discussed in detail in Pacher et al. (2006) Pharmacol. Rev. 58:389-462.

In order to modulate the level of endogenous FAAH substrates, such as anandamide, which in turn modulate the endocannabinoid system, inhibitors of the FAAH enzyme have been developed. This allows conditions and diseases associated with the endocannabinoid system to be at least partially treated or prevented.

Since the substrates of FAAH bind to other receptors, e.g. the vanilloid receptor, and/or are involved in other signalling pathways, inhibitors of FAAH may also allow conditions or diseases associated with other pathways or systems, e.g. the vanilloid system, to be at least partially treated or prevented.

WO 2010/074588 discloses compounds which are inhibitors of FAAH. Käsnänen et al. (Heikki Käsnänen, Mikko J. Myllymäki, Anna Minkkilä, Antti O. Kataja, Susanna M. Saario, Tapio Nevalainen, Ari M. P. Koskinen, and Antti Poso. Chem Med Chem 2010, 5(2), 213-231) discloses carbamate compounds which are FAAH inhibitors. In particular, compound 6b is a FAAH inhibitor which contains an imidazole structure. However, this compound is a weak FAAH inhibitor compared to many of the other carbamate compounds described in this paper and which do not contain an imidazole structure.

SUMMARY OF THE INVENTION

In a first aspect, the present invention provides a compound having a structure selected from the following:

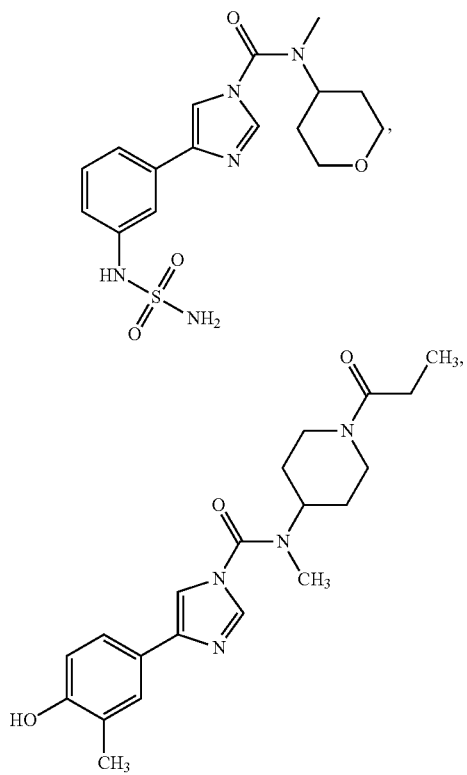

-continued

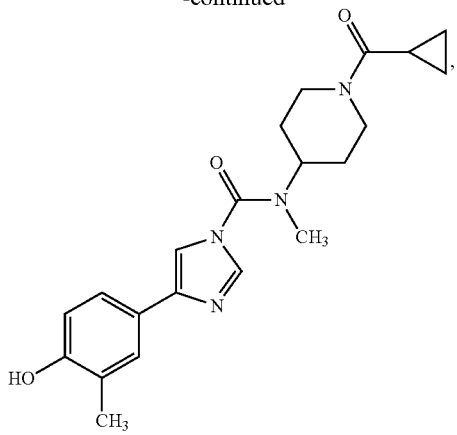

or a pharmaceutically acceptable salt thereof.

The compounds of the invention have been found to modulate the activity of the enzyme fatty acid amide hydrolase (FAAH). Further, they have been shown to be relatively potent, to have relatively high peripheral selectivity (i.e. they inhibit FAAH to a greater extent in peripheral tissue compared to central nervous system tissue) and to be relatively metabolically stable. The compounds of the invention have also been shown to give better results relating to one or more properties compared to the compounds disclosed in WO 2010/074588.

'Pharmaceutically acceptable salts' of the compounds of the present invention include salts with inorganic bases, salts with organic bases, salts with inorganic acids, salts with organic acids and salts with basic or acidic amino acids. Salts with acids may, in particular, be employed in some instances. Exemplary salts include hydrochloride salt, acetate salt, trifluoroacetate salt, methanesulfonate salt, 2-hydroxypropane-1,2,3-tricarboxylate salt, (2R,3R)-2,3-dihydroxysuccinate salt, phosphate salt, sulphate salt, benzoate salt, 2-hydroxy-benzoate salt, S-(+)-mandelate salt, S-(−)-malate salt, S-(−) pyroglutamate salt, pyruvate salt, p-toluenesulfonate salt, 1-R-(−)-camphorsulfonate salt, fumarate salt, maleate salt and oxalate salt. The compounds of the present invention may be in either solvate (e.g. hydrate) or non-solvate (e.g. non-hydrate) form. When in a solvate form, additional solvents may be alcohols such as propan-2-ol.

General methods for the preparation of salts are well known to the person skilled in the art. Pharmaceutical acceptability of salts will depend on a variety of factors, including formulation processing characteristics and in vivo behaviour, and the skilled person would readily be able to assess such factors having regard to the present disclosure.

In accordance with a second aspect of the invention, there is provided a pharmaceutical composition comprising a compound according to the first aspect of the invention, together with one or more pharmaceutically acceptable excipients.

Pharmaceutical compositions of this invention comprise the compound of the first aspect of the present invention with any pharmaceutically acceptable carrier, adjuvant or vehicle. Pharmaceutically acceptable carriers, adjuvants and vehicles that may be used in the pharmaceutical compositions of this invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, rectally, nasally, buccally, vaginally or via an implanted reservoir. Oral administration is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as that described in Ph. Helv, or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

The compounds of the present invention may be administered in a dose of around 1 to around 20,000 µg/kg per dose, for example, around 1 to around 10,000 µg/kg, around 1 to around 5,000 µg/kg, around 1 to around 3,000 µg/kg, around 1 to around 2,000 µg/kg, around 1 to around 1,500 µg/kg, around 1 to around 1,000 µg/kg, around 1 to around 500 µg/kg, around 1 to around 250 µg/kg, around 1 to around 100 µg/kg, around 1 to around 50 µg/kg or around 1 to around 25 µg/kg per dose depending on the condition to be treated or prevented, and the characteristics of the subject being administered with the compound. In many instances, the dose may be around 1 to around 10 µg/kg per dose. In particular embodiments, the dose may be around 250 µg/kg per dose, around 100 µg/kg, around 50 µg/kg or around 10 µg/kg per dose. The dosing regimen for a given compound could readily be determined by the skilled person having access to this disclosure.

In one particular embodiment, the pharmaceutical composition of the invention additionally comprises one or more additional active pharmaceutical ingredients. The compound of the invention may be administered with one or more additional active pharmaceutical ingredients, such as anandamide, oleoyl ethanolamide or palmitoyl ethanolamide. This may be in the form of a single composition comprising the compound of the invention and one or more additional active pharmaceutical ingredients. Alternatively, this may be in two or more separate compositions where the compound of the invention is contained in one composition and the one or more additional active pharmaceutical ingredients are contained in one or more separate compositions.

Administration of the compounds of the present invention may therefore be simultaneous with, or staggered with respect to, the one or more additional active pharmaceutical ingredient.

In a third aspect, the present invention provides a compound according to the first aspect of the invention, or a composition according to the second aspect, for use in therapy.

In a fourth aspect, the invention provides a compound according to the first aspect of the invention, or a composition according to the second aspect, for use in the treatment or prevention of a condition whose development or symptoms are linked to a substrate of the FAAH enzyme.

The invention also provides the use of a compound according to the first aspect of the invention, or a composition according to the second aspect, in the manufacture of a medicament for the treatment or prevention of a condition whose development or symptoms are linked to a substrate of the FAAH enzyme.

A number of conditions whose development or symptoms are linked to a substrate of the FAAH enzyme are known to the skilled person. Some of these are discussed above.

In a fifth aspect, the invention also provides a method of treatment or prevention of a condition whose development or symptoms are linked to a substrate of the FAAH enzyme, the method comprising the administration, to a subject in need of such treatment or prevention, of a therapeutically effective amount of a compound according to the first aspect of the invention, or a composition according to the second aspect.

A compound according to the fourth aspect, or a method according to the fifth aspect, wherein the condition is a disorder associated with the endocannabinoid system.

In certain embodiments, the condition to be treated may be selected from:

(i) pain, in particular acute or chronic neurogenic pain such as migraine and neuropathic pain (for example diabetic neuropathic pain, post-herpetic neuralgia, trigeminal neuralgia); migraine; acute or chronic inflammatory pain, such as that associated with inflammatory diseases such as arthritis, rheumatoid arthritis, osteoarthritis, osteoporosis, spondylitis, gout, vasculitis, Crohn's disease, and irritable bowel syndrome; acute or chronic peripheral pain; cancer pain;

(ii) dizziness, vomiting, and nausea, in particular resulting from chemotherapy;

(iii) eating disorders, in particular appetite disorders, metabolic disorders, anorexia and cachexia of various natures;

(iv) neurological and psychiatric pathologies such as tremors, dyskinesias, dystonias, nausea, emesis, addictive disorders (such as addiction to a drug(s) or alcohol), spasticity, obsessive-compulsive behaviour, Tourette's syndrome, all forms of depression and anxiety of any nature and origin, insomnia, mood disorders, and psychoses such as schizophrenia;

(v) acute and chronic neurodegenerative diseases such as Parkinson's disease, Alzheimer's disease, senile dementia, Huntington's chorea, lesions related to cerebral ischaemia and to cranial and medullary trauma;

(vi) epilepsy;

(vii) sleep disorders, including sleep apnoea;

(viii) cardiovascular diseases such as heart failure, hypertension, circulatory shock, myocardial reperfusion injury, cardiac arrhythmias, arteriosclerosis/atherosclerosis, heart attack, cardiac ischaemia, vasculitis and renal ischaemia;

(ix) cancers, for example benign skin tumours, brain tumours and papillomas, prostate tumours, and cerebral tumours (glioblastomas, medulloepitheliomas, medulloblastomas, neuroblastomas, tumours of embryonic origin, astrocytomas, astroblastomas, ependymomas, oligodendrogliomas, plexus tumour, neuroepitheliomas, epiphyseal tumour, ependymoblastomas, malignant meningiomas, sarcomatosis, malignant melanomas, and schwannomas);

(x) disorders of the immune system, in particular autoimmune diseases, such as psoriasis, lupus erythematosus, diseases of the connective tissue or collagen diseases, Sjögren's syndrome, ankylosing spondylitis, undifferentiated spondylitis, Behcet's disease, autoimmune haemolytic anaemia, multiple sclerosis, amylotrophic lateral sclerosis, amyloidosis, graft rejection, diseases affecting the plasmacytic line, allergic diseases; immediate or delayed hypersensitivity, allergic rhinitis or conjunctivitis, contact dermatitis;

(xi) parasitic, viral or bacterial infectious diseases such as AIDS, and meningitis;

(xii) inflammatory diseases, in particular joint diseases such as arthritis, rheumatoid arthritis, osteoarthritis, spondylitis, gout, vasculitis, Crohn's disease, irritable/inflammatory bowel syndrome, asthma;

(xiii) osteoporosis;

(xiv) eye conditions such as ocular hypertension, retinopathy and glaucoma;

(xv) pulmonary conditions including diseases of the respiratory tracts, bronchospasm, coughing, asthma, chronic bronchitis, chronic obstruction of the respiratory tract, and emphysema;

(xvi) gastrointestinal diseases such as irritable/inflammatory bowel syndrome, inflammatory intestinal disorders, ulcers, diarrhoea, urinary incontinence and bladder inflammation;
(xvii) acute and chronic liver diseases such as hepatitis and cirrhosis;
(xviii) neurological disorders such as neurotrauma, stroke, multiple sclerosis, spinal cord injury, Parkinson's disease, levodopa-induced diskinesia, Huntington's disease/chorea, Gilles de la Tourette, tardive diskinesia, dystonia, amytrophic lateral sclerosis, Alzheimer's disease, and epilepsy.

DETAILED DESCRIPTION OF THE INVENTION

The invention will now be described in more detail by way of example only:

1. Synthetic Methodologies

The methods used for synthesis of the compounds of the invention are illustrated by the general schemes and specific syntheses below. All compounds and intermediates were characterised by nuclear magnetic resonance (NMR). The starting materials and reagents used in preparing these compounds are available from commercial suppliers or can be prepared by methods obvious to those skilled in the art. These general schemes and specific syntheses are merely illustrative of methods by which the compounds of this invention can be synthesised, and various modifications to these schemes and syntheses can be made and will be suggested to one skilled in the art having referred to this disclosure.

The compounds of the invention were characterised by melting point and NMR. NMR spectra were recorded on a Bruker Avance III 600 MHz spectrometer with solvent used as internal standard. 13C spectra were recorded at 150 MHz and 1H spectra were recorded at 600 MHz. Data are reported in the following order: approximate chemical shift (ppm), number of protons, multiplicity (br, broad; d, doublet; m, multiplet; s, singlet; t; triplet) and coupling constant (Hz).

Room temperature in the following schemes means the temperature ranging from 20° C. to 25° C.

1.1. General Scheme for the Synthesis of N-Methyl-4-(3-(sulfamoylamino)phenyl)-N-(tetrahydro-2H-pyran-4-yl)-1H-imidazole-1-carboxamide (Compound 1)

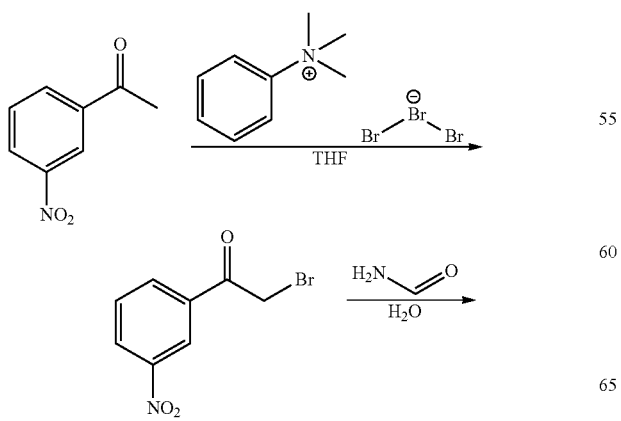

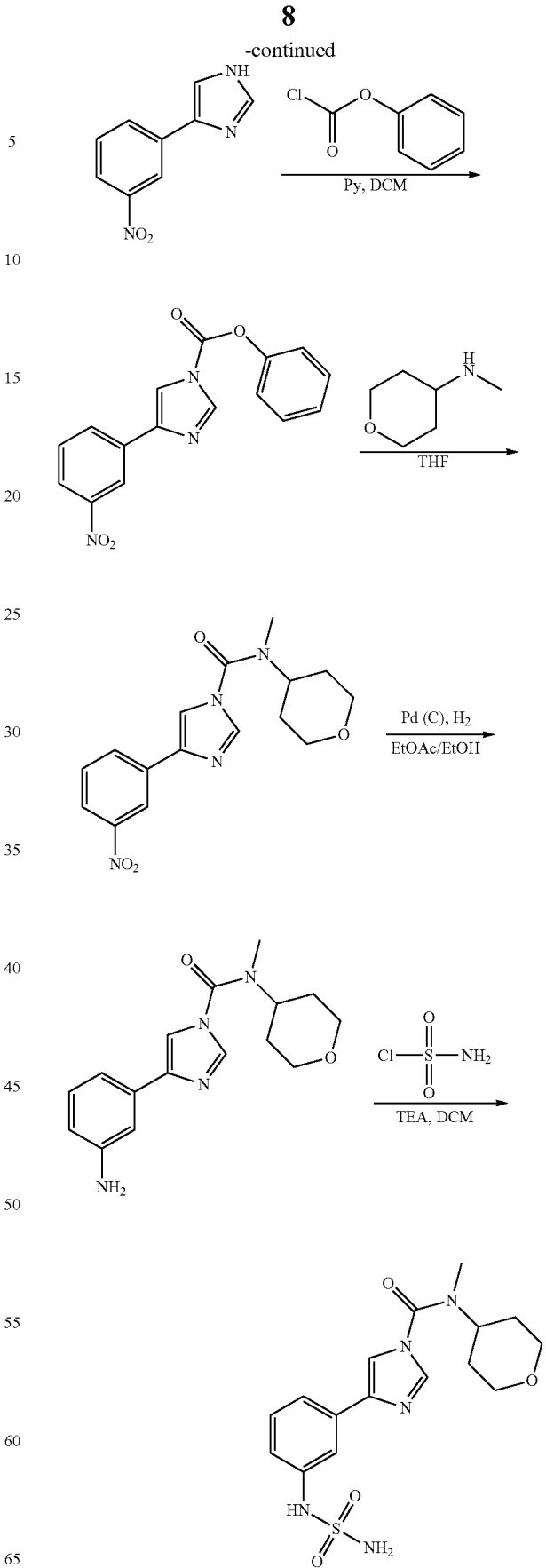

Phenyl 4-(3-nitrophenyl)-1H-imidazole-1-carboxylate

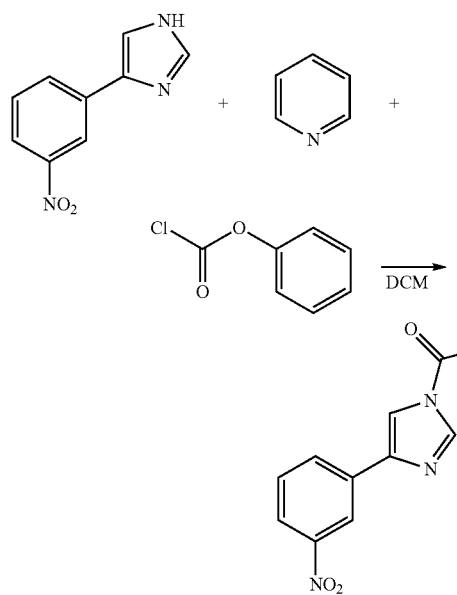

Phenyl carbonochloridate (3.2 mL, 25.4 mmol) was added to a stirred solution of 4-(3-nitrophenyl)-1H-imidazole (4 g, 21.1 mmol) and pyridine (2.0 mL, 25.4 mmol) in DCM (100 mL) at 0° C. The reaction mixture was allowed to stir at room temperature for 2 h. Water was added and the organic layer was separated, dried (MgSO₄) and evaporated in vacuum to give a beige solid. The solid was then recrystallised from a mixture of propan-2-ol and DCM and the product was isolated as a beige solid. Phenyl 4-(3-nitrophenyl)-1H-imidazole-1-carboxylate (2.89 g, 44% yield).

N-Methyl-4-(3-nitrophenyl)-N-(tetrahydro-2H-pyran-4-yl)-1H-imidazole-1-carboxamide

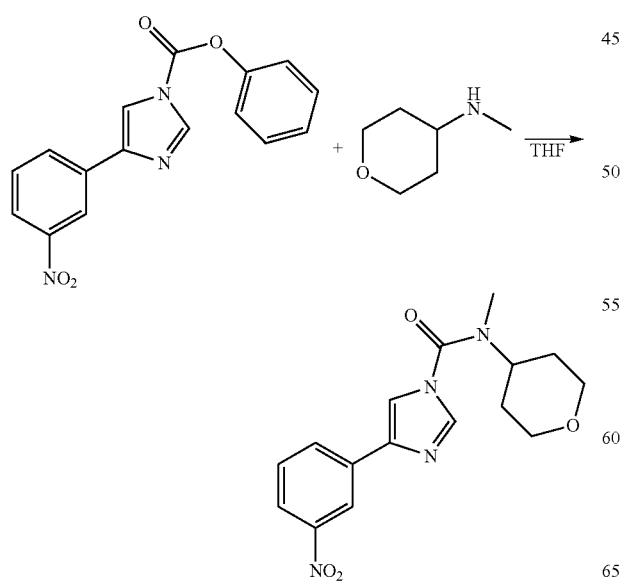

A solution of N-methyltetrahydro-2H-pyran-4-amine (2.15 g, 18.7 mmol) in tetrahydrofuran (THF) (6 mL) was added to a stirred solution of phenyl 4-(3-nitrophenyl)-1H-imidazole-1-carboxylate (2.89 g, 9.3 mmol) in THF (40 mL) at room temperature. The yellow solution was allowed to stir at reflux overnight. The solvent was evaporated in vacuum and the product was recrystallised from propan-2-ol. N-methyl-4-(3-nitrophenyl)-N-(tetrahydro-2H-pyran-4-yl)-1H-imidazole-1-carboxamide (0.938 g, 30% yield).

4-(3-Aminophenyl)-N-methyl-N-(tetrahydro-2H-pyran-4-yl)-1H-imidazole-1-carboxamide

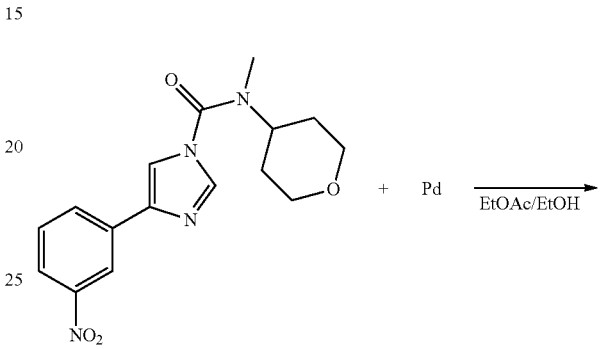

A mixture of ethanol (30.0 mL) and ethyl acetate (30 mL) was added to wet palladium (0.151 g, 0.142 mmol, 10% on activated charcoal) under an atmosphere of argon. To this mixture was added N-methyl-4-(3-nitrophenyl)-N-(tetrahydro-2H-pyran-4-yl)-1H-imidazole-1-carboxamide (0.938 g, 2.84 mmol) and the suspension was allowed to stir at room temperature overnight under an atmosphere of hydrogen. The resultant grey suspension was filtered through celite and the celite was washed with DCM. The filtrate was evaporated in vacuum and the colourless product was recrystallised from propan-2-ol. 4-(3-Aminophenyl)-N-methyl-N-(tetrahydro-2H-pyran-4-yl)-1H-imidazole-1-carboxamide (0.695 g, 81% yield).

N-Methyl-4-(3-(sulfamoylamino)phenyl)-N-(tetrahydro-2H-pyran-4-yl)-1H-imidazole-1-carboxamide (Compound 1)

1.2. General Scheme for the Synthesis of 4-(4-methoxy-3-methylphenyl)-N-methyl-N-(piperidin-4-yl)-1H-imidazole-1-carboxamide hydrochloride (Intermediate 1)

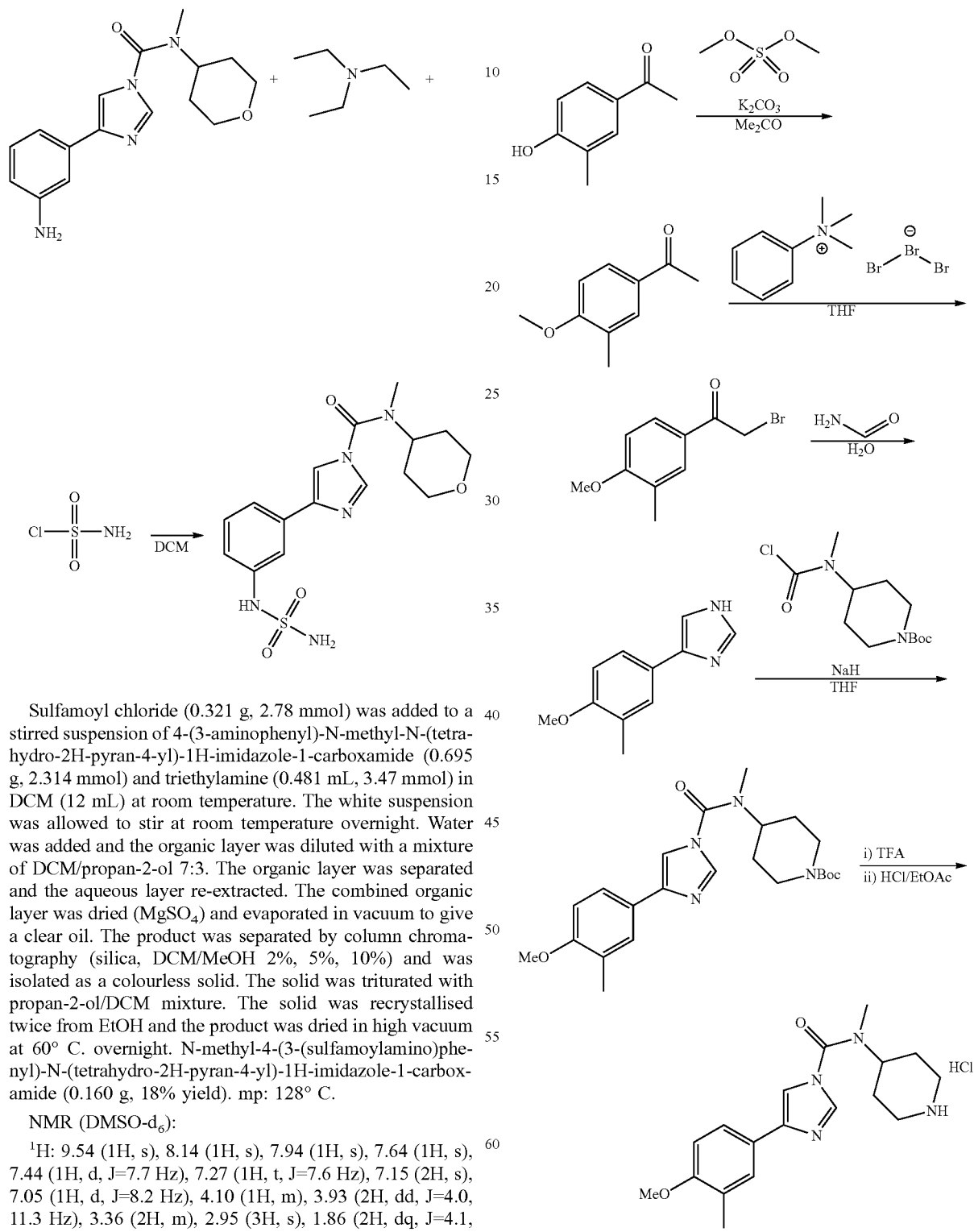

Sulfamoyl chloride (0.321 g, 2.78 mmol) was added to a stirred suspension of 4-(3-aminophenyl)-N-methyl-N-(tetrahydro-2H-pyran-4-yl)-1H-imidazole-1-carboxamide (0.695 g, 2.314 mmol) and triethylamine (0.481 mL, 3.47 mmol) in DCM (12 mL) at room temperature. The white suspension was allowed to stir at room temperature overnight. Water was added and the organic layer was diluted with a mixture of DCM/propan-2-ol 7:3. The organic layer was separated and the aqueous layer re-extracted. The combined organic layer was dried (MgSO$_4$) and evaporated in vacuum to give a clear oil. The product was separated by column chromatography (silica, DCM/MeOH 2%, 5%, 10%) and was isolated as a colourless solid. The solid was triturated with propan-2-ol/DCM mixture. The solid was recrystallised twice from EtOH and the product was dried in high vacuum at 60° C. overnight. N-methyl-4-(3-(sulfamoylamino)phenyl)-N-(tetrahydro-2H-pyran-4-yl)-1H-imidazole-1-carboxamide (0.160 g, 18% yield). mp: 128° C.

NMR (DMSO-d$_6$):

$^1$H: 9.54 (1H, s), 8.14 (1H, s), 7.94 (1H, s), 7.64 (1H, s), 7.44 (1H, d, J=7.7 Hz), 7.27 (1H, t, J=7.6 Hz), 7.15 (2H, s), 7.05 (1H, d, J=8.2 Hz), 4.10 (1H, m), 3.93 (2H, dd, J=4.0, 11.3 Hz), 3.36 (2H, m), 2.95 (3H, s), 1.86 (2H, dq, J=4.1, 12.3 Hz), 1.70 (2H, d, J=12.0 Hz).

$^{13}$C: 151, 140.6, 139.9, 137.5, 134, 129, 118.6, 116.9, 114.6, 114.4, 66.3, 54.2, 31.6, 29.1.

1-(4-Methoxy-3-methylphenyl)ethanone

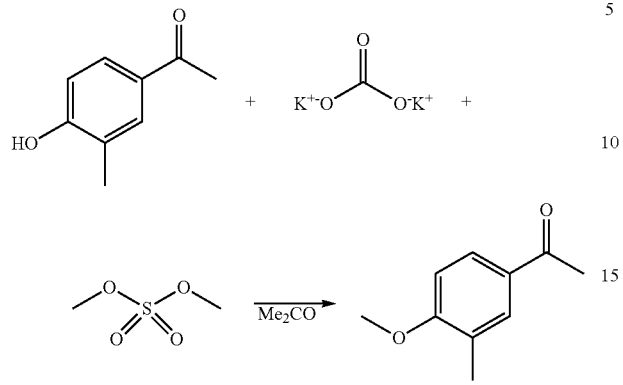

Dimethyl sulfate (17.50 mL, 183 mmol) was added to a stirred suspension of 1-(4-hydroxy-3-methylphenyl)ethanone (25 g, 166 mmol) and potassium carbonate (28.8 g, 208 mmol) in acetone (277 mL) at room temperature. The suspension was allowed to stir at reflux overnight. The solid was separated by filtration and was washed with acetone and the filtrate was evaporated in vacuum. The organic residue was dissolved in EtOAc and was washed with water. The organic layer was separated, dried (MgSO$_4$) and evaporated in vacuum to give a yellow oil. Used without further purification. 1-(4-Methoxy-3-methylphenyl)ethanone (28.7 g).

2-Bromo-1-(4-methoxy-3-methylphenyl)ethanone

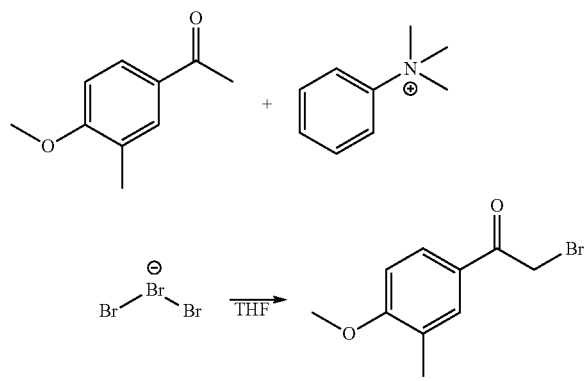

A solution of phenyltrimethylammonium tribromide (30.2 g, 80 mmol) in THF (122 mL) was added dropwise to a stirred solution of 1-(4-methoxy-3-methylphenyl)ethanone (12 g, 73.1 mmol) in THF (122 mL) at room temperature. The yellow suspension was allowed to stir at room temperature for 1 h. The solid was separated by filtration and was washed with THF. The filtrate was evaporated in vacuum and the organic residue was dissolved in EtOAc and was washed with water. The organic layer was dried (MgSO$_4$) and evaporated in vacuum to give a violet oil. Used without further purification. 2-Bromo-1-(4-methoxy-3-methylphenyl)ethanone (27.9 g).

4-(4-methoxy-3-methylphenyl)-1H-imidazole

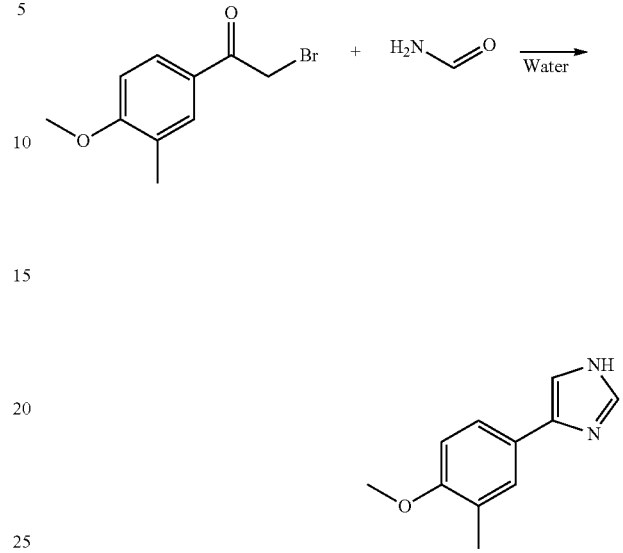

Water (4 mL) was added to a stirred suspension of 2-bromo-1-(4-methoxy-3-methylphenyl)ethanone (27.9 g, 115 mmol) and formamide (56.7 mL, 1423 mmol) at room temperature. The suspension was allowed to stir at 140° C. for 5 h. The mixture was poured into 200 mL of water to give a dark dense brown oil. The oil was separated by filtration and was washed with 1N HCl and the filtrate was basified with NaOH 50% to give a beige solid. The solid was separated by filtration and was washed with diethyl ether (5×) to give an off-white solid. 4-(4-Methoxy-3-methylphenyl)-1H-imidazole (5.2 g, 24% yield).

tert-Butyl 4-(methylamino)piperidine-1-carboxylate

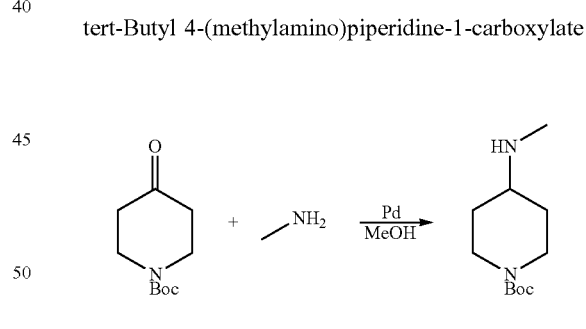

A solution of methanamine (38.0 mL, 442 mmol, 40% aqueous solution) in methanol (100 mL) was added to wet palladium (1.602 g, 1.506 mmol, 10% on activated charcoal) at room temperature under an atmosphere of argon. To this mixture was added tert-butyl 4-oxopiperidine-1-carboxylate (20 g, 100 mmol) portionwise and the mixture was allowed to stir at 50° C., 20 bar over 1 h. The suspension was flushed with argon and was filtered through celite and the celite was washed with DCM. The filtrate was evaporated in vacuum to give the product as a clear oil. The oil was dissolved in EtOAc and was washed with water. The organic layer was dried (MgSO$_4$) and evaporated in vacuum to give a clear oil. Used without further purification. tert-Butyl 4-(methylamino)piperidine-1-carboxylate (20 g, 93% yield).

tert-Butyl 4-(chlorocarbonyl(methyl)amino)piperidine-1-carboxylate

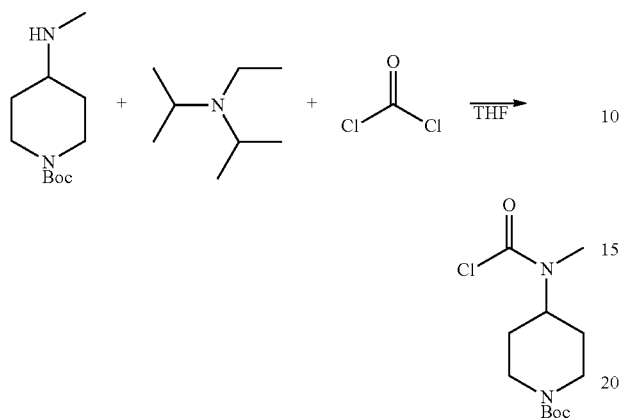

A solution of tert-butyl 4-(methylamino)piperidine-1-carboxylate (20 g, 93 mmol) and Hunig's base (35.9 mL, 205 mmol) in THF (133 mL) was added dropwise to stirred phosgene (53.3 mL, 112 mmol, 20% solution in toluene) at 0° C. to give a white suspension. The mixture was allowed to stir at 0° C. for 10 min and at room temperature for 2 h. The suspension was poured into ice/water and the organic residue was extracted with EtOAc. The organic layer was separated and washed with 1N HCl solution. The organic layer was dried (MgSO$_4$) and evaporated in vacuum to give a yellow oil. The oil was triturated with a mixture of PE and few drops of diethyl ether to give a colourless solid. The solid was separated by filtration and was washed with petroleum ether. tert-Butyl 4-(chlorocarbonyl(methyl)amino)piperidine-1-carboxylate (17.4 g, 67% yield).

tert-Butyl 4-(4-(4-methoxy-3-methylphenyl)-N-methyl-1H-imidazole-1-carboxamido)piperidine-1-carboxylate

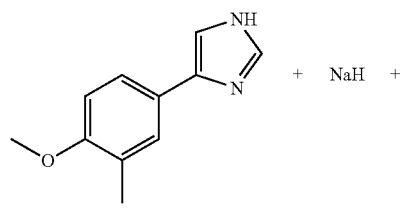

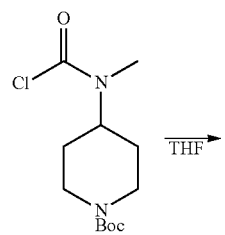

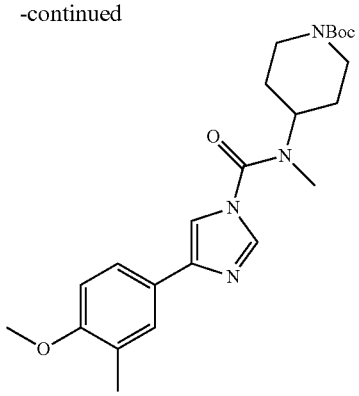

Sodium hydride (1.313 g, 32.8 mmol, 60% dispersion in oil) was added portionwise to a stirred suspension of 4-(4-methoxy-3-methylphenyl)-1H-imidazole (5.15 g, 27.4 mmol) in THF (137 mL) at 0° C. The dark blue solution was allowed to stir at room temperature for 30 min and then tert-butyl 4-(chlorocarbonyl(methyl)amino)piperidine-1-carboxylate (11.36 g, 41.0 mmol) was added at 0° C. to give a dark solution. The mixture was allowed to stir at room temperature for 2 h. Water was added at 0° C. and the organic layer was diluted with a mixture of DCM/propan-2-ol 7:3. The organic layer was separated, dried (MgSO$_4$) and evaporated in vacuum to give a beige solid. The solid was recrystallised from propan-2-ol tert-Butyl 4-(4-(4-methoxy-3-methylphenyl)-N-methyl-1H-imidazole-1-carboxamido)piperidine-1-carboxylate (9.39 g, 80% yield).

4-(4-Methoxy-3-methylphenyl)-N-methyl-N-(piperidin-4-yl)-1H-imidazole-1-carboxamide hydrochloride

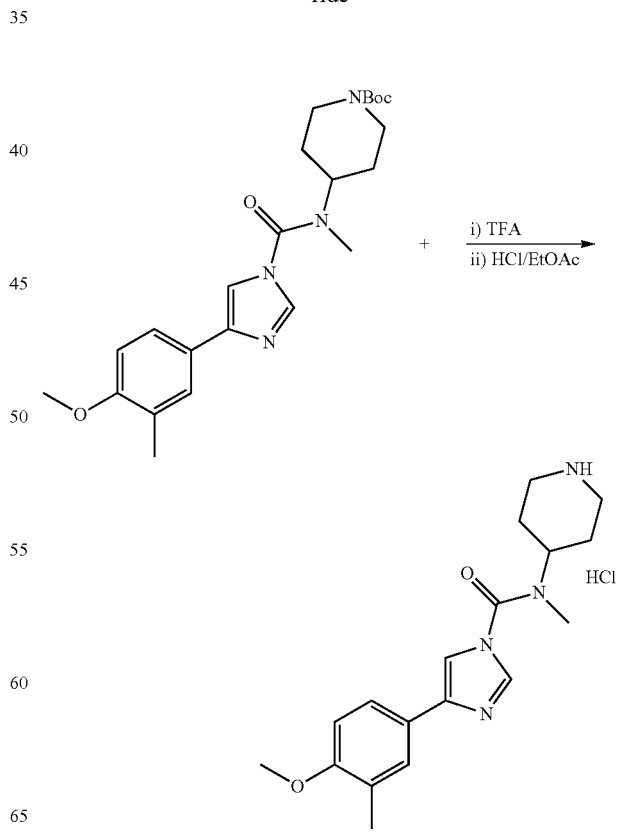

TFA (30 mL) was carefully added to the residue tert-butyl 4-(4-(4-methoxy-3-methylphenyl)-N-methyl-1H-imidazole-1-carboxamido)piperidine-1-carboxylate (9.39 g, 21.91 mmol) at room temperature. The yellow solution was allowed to stir at room temperature for 1.5 h. The TFA was evaporated in vacuum and then was azeotroped twice with toluene. The yellow residue was then dissolved in ethyl acetate (30 mL) and a 2M solution of hydrogen chloride (32.9 mL, 65.7 mmol) in diethyl ether was added dropwise at 0° C. to give a white suspension. The mixture was allowed to stir at room temperature for 30 min and then the solid was separated by filtration and was washed with EtOAc. 4-(4-Methoxy-3-methylphenyl)-N-methyl-N-(piperidin-4-yl)-1H-imidazole-1-carboxamide hydrochloride (11.06 g).

1.3. General Scheme for the Synthesis of 4-(4-Hydroxy-3-methylphenyl)-N-methyl-N-(1-propionylpiperidin-4-yl)-1H-imidazole-1-carboxamide (Compound 2)

4-(4-Methoxy-3-methylphenyl)-N-methyl-N-(1-propionylpiperidin-4-yl)-1H-imidazole-1-carboxamide

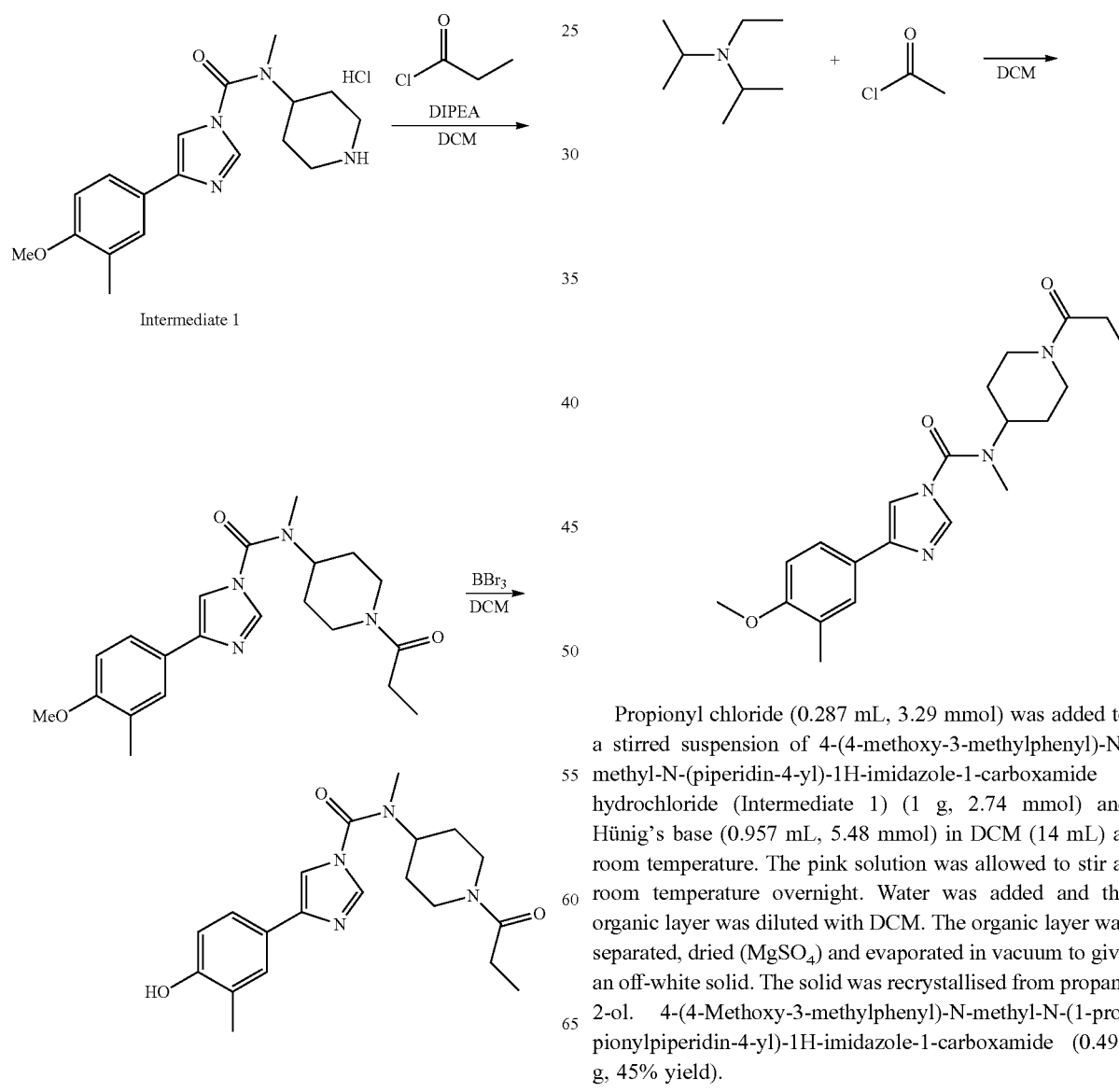

Propionyl chloride (0.287 mL, 3.29 mmol) was added to a stirred suspension of 4-(4-methoxy-3-methylphenyl)-N-methyl-N-(piperidin-4-yl)-1H-imidazole-1-carboxamide hydrochloride (Intermediate 1) (1 g, 2.74 mmol) and Hünig's base (0.957 mL, 5.48 mmol) in DCM (14 mL) at room temperature. The pink solution was allowed to stir at room temperature overnight. Water was added and the organic layer was diluted with DCM. The organic layer was separated, dried (MgSO$_4$) and evaporated in vacuum to give an off-white solid. The solid was recrystallised from propan-2-ol. 4-(4-Methoxy-3-methylphenyl)-N-methyl-N-(1-propionylpiperidin-4-yl)-1H-imidazole-1-carboxamide (0.496 g, 45% yield).

4-(4-Hydroxy-3-methylphenyl)-N-methyl-N-(1-propionylpiperidin-4-yl)-1H-imidazole-1-carboxamide (Compound 2)

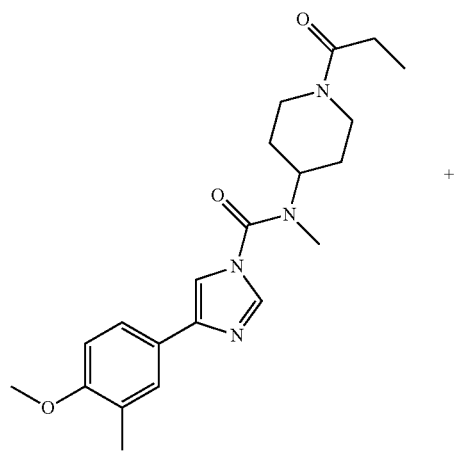

product was separated by column chromatography (silica, DCM/MeOH 2%, 5%, 10%) and was isolated as a colourless solid. The solid was recrystallised from propan-2-ol. 4-(4-Hydroxy-3-methylphenyl)-N-methyl-N-(1-propionylpiperidin-4-yl)-1H-imidazole-1-carboxamide (0.22 g, 45% yield). mp: 232° C.

NMR (DMSO-$d_6$):

$^1$H: 9.34 (1H, s), 8.06 (1H, d, J=1.2 Hz), 7.77 (1H, d, J=1.2 Hz), 7.55 (1H, d, J=1.6 Hz), 7.47 (1H, dd, J=2, 8.3 Hz), 6.77 (1H, d, J=8.3 Hz), 4.53 (1H, d, J=12.5 Hz), 4.10 (1H, m), 3.95 (1H, d, J=13.5 Hz), 3.06 (1H, mt, J=13.0 Hz), 2.91 (3H, s), 2.56 (1H, mt, J=12.8 Hz), 2.34 (2H, q, J=7.5 Hz), 2.14 (3H, s), 1.76 (3H, m), 1.60 (1H, dq, J=4.3, 12.3 Hz), 0.98 (3H, t, J=7.5 Hz).

$^{13}$C: 171.1, 154.8, 151.1, 141.1, 137.3, 127.3, 124.2, 123.8, 123.4, 114.6, 112.3, 55.1, 43.9, 40.3, 31.6, 28.6, 28, 25.5, 16.1, 9.5.

1.4 General Scheme for the Synthesis of N-(1-(Cyclopropanecarbonyl)piperidin-4-yl)-4-(4-hydroxy-3-methylphenyl)-N-methyl-1H-imidazole-1-carboxamide (Compound 3)

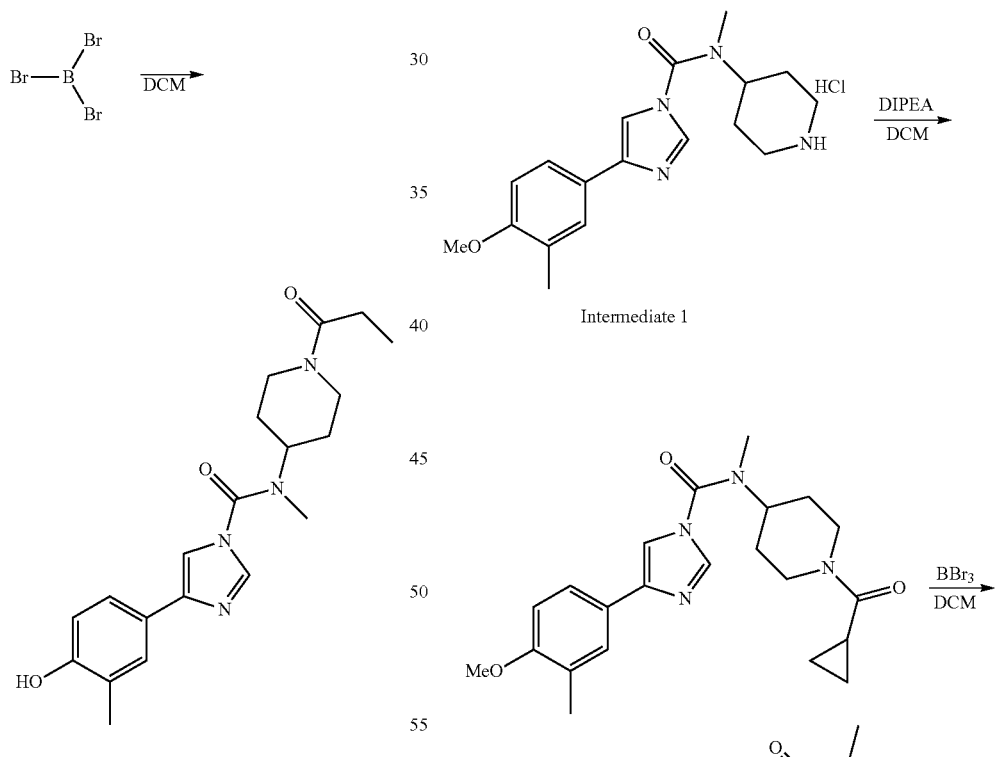

Boron tribromide (0.354 mL, 3.75 mmol) was added to a stirred suspension of 4-(4-methoxy-3-methylphenyl)-N-methyl-N-(1-propionylpiperidin-4-yl)-1H-imidazole-1-carboxamide (0.480 g, 1.248 mmol) in anhydrous DCM (4 mL) at −78° C. The suspension was allowed to stir at −78° C. for 15 min and at room temperature for 2 h. Water was added at −50° C. and then the organic layer was diluted with a mixture of DCM/propan-2-ol 7:3. The organic layer was separated; the aqueous layer was saturated with NaCl and re-extracted. The combined organic layer was dried (MgSO$_4$) and evaporated in vacuum to give a clear oil. The

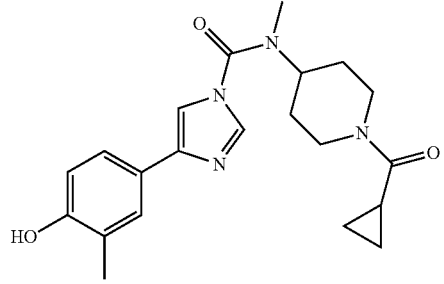

21
N-(1-(Cyclopropanecarbonyl)piperidin-4-yl)-4-(4-methoxy-3-methylphenyl)-N-methyl-1H-imidazole-1-carboxamide

22
N-(1-(Cyclopropanecarbonyl)piperidin-4-yl)-4-(4-hydroxy-3-methylphenyl)-N-methyl-1H-imidazole-1-carboxamide (Compound 3)

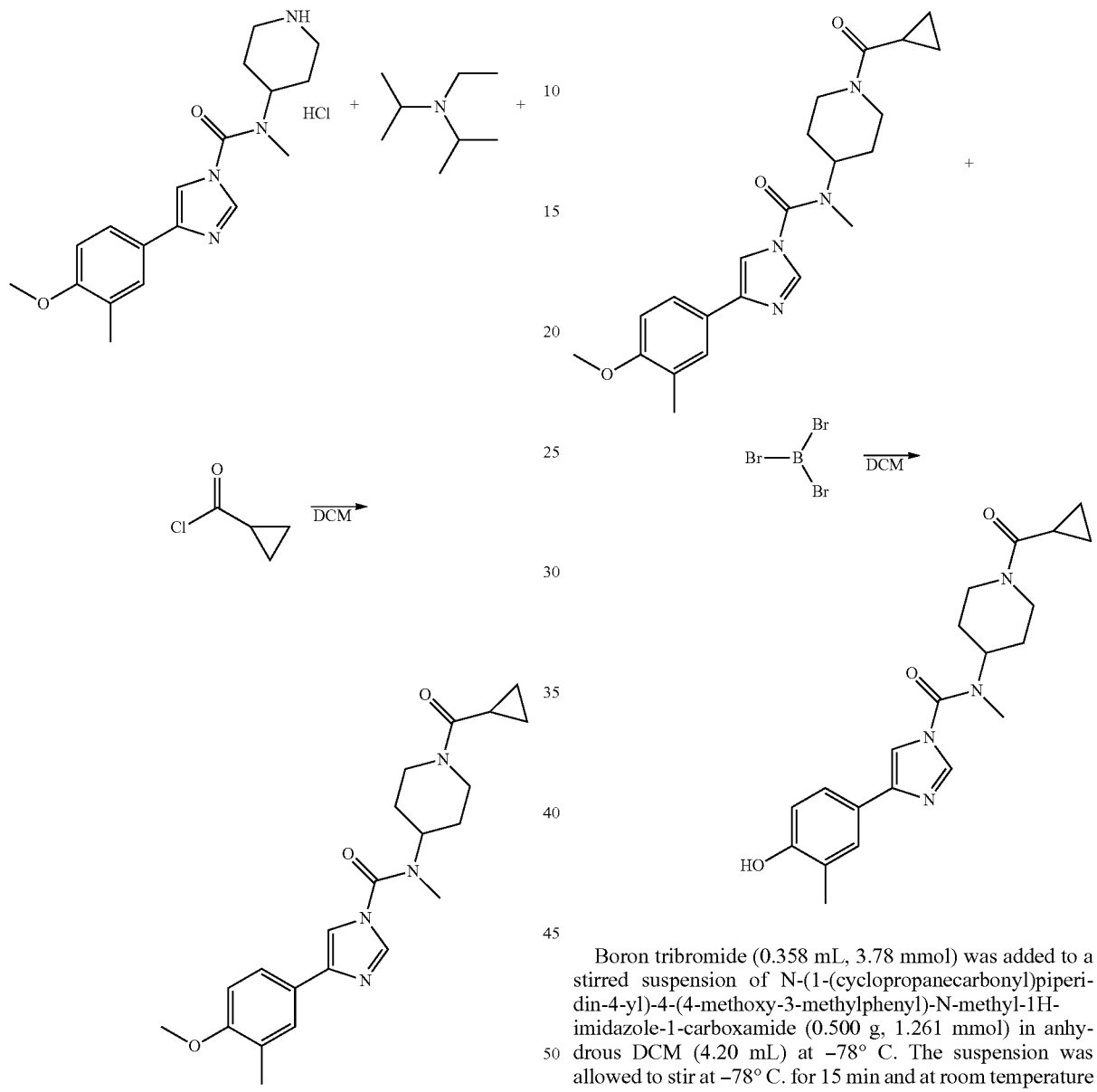

Cyclopropanecarbonyl chloride (1.5 mL, 16.44 mmol) was added to a stirred suspension of 4-(4-methoxy-3-methylphenyl)-N-methyl-N-(piperidin-4-yl)-1H-imidazole-1-carboxamide hydrochloride (Intermediate 1) (5 g, 13.70 mmol) and Hunig's base (4.8 mL, 27.4 mmol) in DCM (70 mL) at room temperature. The pink solution was allowed to stir at room temperature overnight to give a pink suspension. Water was added and the organic layer was diluted with DCM. The organic layer was separated, dried (MgSO₄) and evaporated in vacuum to give clear oil that solidified into an off-white solid. The solid was recrystallised from propan-2-ol. N-(1-(Cyclopropanecarbonyl)piperidin-4-yl)-4-(4-methoxy-3-methylphenyl)-N-methyl-1H-imidazole-1-carboxamide (2.96 g, 55% yield).

Boron tribromide (0.358 mL, 3.78 mmol) was added to a stirred suspension of N-(1-(cyclopropanecarbonyl)piperidin-4-yl)-4-(4-methoxy-3-methylphenyl)-N-methyl-1H-imidazole-1-carboxamide (0.500 g, 1.261 mmol) in anhydrous DCM (4.20 mL) at −78° C. The suspension was allowed to stir at −78° C. for 15 min and at room temperature for 2 h. Water was added at −50° C. and then the organic layer was diluted with a mixture of DCM/propan-2-ol 7:3. The organic layer was separated; the aqueous layer was saturated with NaCl and re-extracted. The combined organic layer was dried (MgSO₄) and evaporated in vacuum to give a clear oil. The product was separated by column chromatography (silica, DCM/MeOH 2%, 5%, 10%) and was isolated as a colourless solid. The solid was recrystallised from a mixture of propan-2-ol and DCM. N-(1-(Cyclopropanecarbonyl)piperidin-4-yl)-4-(4-hydroxy-3-methylphenyl)-N-methyl-1H-imidazole-1-carboxamide (0.289 g, 57% yield). mp: 204° C.

NMR (DMSO-d₆):
$^1$H: 9.32 (1H, s), 8.06 (1H, d, J=1.2 Hz), 7.76 (1H, d, J=1.2 Hz), 7.55 (1H, d, J=1.6 Hz), 7.47 (1H, dd, J=2, 8.2 Hz), 6.77 (1H, d, J=8.2 Hz), 4.51 (1H, d, J=12.0 Hz), 4.37

(1H, d, J=13.0 Hz), 4.13 (1H, m), 3.15 (1H, t, J=13.0 Hz), 2.92 (3H, s), 2.61 (1H, mt, J=13.0 Hz), 2.14 (3H, s), 2.0 (1H, m), 1.85 (1H, md), 1.77 (2H, m), 1.63 (1H, mq), 0.8-0.66 (4H, m).

$^{13}$C: 170.8, 154.8, 151.2, 141.1, 137.3, 127.3, 124.2, 123.8, 123.4, 114.6, 112.4, 55.2, 44, 40.8, 31.7, 28.9, 28, 16.1, 10.3, 7, 6.9.

2. Biological Efficacy

All animal procedures were conducted in strict adherence to the European Directive for Protection of Vertebrate Animals Used for Experimental and Other Scientific Purposes (86/609CEE) and Portuguese legislation (Decreto-Lei 129/92, Portarias 1005/92 e 1131/97). The number of animals used was the minimum possible in compliance with current regulations and scientific integrity.

In vivo testing was performed according to the protocol described below. BRh (brain homogenate) indicates inhibition in central nervous tissue, in this case, brain, and LVh (liver homogenate) indicates inhibition in peripheral tissue, in this case, liver. The controls were the reaction mix minus the test compounds. Therefore, a low value for the test compound indicates a strong inhibitor. A value of 100 indicates that no measurable inhibition took place.

In Vivo Protocols
Experiments in Mice
Animal Treatment

The animals used for experiments were male NMRI mice (weighing 27-44 g) obtained from Interfauna Ibérica (Spain). Mice were kept 5 per cage, under controlled environmental conditions (12 hr light/dark cycle and room temperature 22±1° C.). Food and tap water were allowed ad libitum and the experiments were all carried out during daylight hours.

Animals were always fasted overnight before administration of compounds.

Animals were administered the appropriate dose of the compound of the invention via oral route (8 ml/kg; compound suspended in 0.5% carboxymethylcellulose (CMC) or solubilized in water) or vehicle (controls) using animal feeding stainless steel curve needles (Perfectum, U.S.A.). Fifteen minutes before sacrifice animal were anesthetized with pentobarbital 60 mg/kg administered intraperitoneally. A fragment of liver and brain without cerebellum were removed and put in plastic vials containing membrane buffer (3 mM $MgCl_2$, 1 mM EDTA, 50 mM Tris HCl pH 7.4). Tissues were stored at −30° C. until analysis.

Reagents and Solutions

Anandamide [ethanolamine-1-$^3$H-] (40-60 Ci/mmol) was obtained from American Radiochemicals. All other reagents were obtained from Sigma-Aldrich. Optiphase Supermix was obtained from Perkin Elmer and activated charcoal was obtained from Sigma-Aldrich.

Tissue Preparation

Tissues were thawed on ice and were homogenized in 10 volumes of membrane buffer (3 mM $MgCl_2$, 1 mM EDTA, 50 mM Tris HCl pH 7.4) with either Potter-Elvejhem (brains—8 strokes at 500 rpm) or Heidolph Diax (livers—2 strokes at position 5 for 20 sec with 30 sec pauses).

Total protein in tissues was determined with the BioRad Protein Assay (BioRad) using a standard curve of BSA (50-250 μg/ml).

Enzymatic Assay

Reaction mix (total volume of 200 μl) contained: 2 μM AEA (2 μM AEA+5 nM $^3$H-AEA), 0.1% fatty acid free BSA, 15 μg (brain) or 5 μg (liver) protein, in 1 mM EDTA, 10 mM Tris pH 7.6. After a 15 min pre-incubation period at 37° C., reaction was started by the addition of the substrate solution (cold AEA+radiolabelled AEA+BSA). Reaction was carried out for 10 min (brain) or 7 min (liver) before termination by the addition of 400 μl activated charcoal suspension (8 g charcoal in 32 ml 0.5 M HCl in continuous agitation). After a 30 min incubation period at room temperature with agitation, charcoal was sedimented by centrifugation in microfuge (10 min at 13000 rpm). 200 μl of the supernatant were added to 800 μl Optiphase Supermix scintillation cocktail previously distributed in 24-well plates. Counts per minute (cpm) were determined in a MicrobetaTriLux scintillation counter.

In each assay blanks (without protein) were prepared.

The percentage of remaining enzymatic activity was calculated with respect to controls and after blank subtraction.

Experiments in Rats
Animal Treatment

Male Wistar rats (body weight range: 190-230 g) were obtained from Harlan (Spain). Rats were kept 5 per cage, under controlled environmental conditions (12 hr light/dark cycle and room temperature 22±1° C.). Food and tap water were allowed ad libitum and the experiments were all carried out during daylight hours.

Rats were administered the appropriate dose of compound of the invention via gavage (administration volume=4 ml/kg body weight) using animal feeding stainless steel curve needles (Perfectum, U.S.A.). Vehicle was 0.5% CMC in Milli Q water. Rats were fasted at least 15 h before experiments.

Fifteen minutes before sacrifice animals were anesthetized with pentobarbital i.p. 60 mg/kg body weight. Liver biopsies and brain samples (without cerebellum) were collected and placed in a plastic vial containing membrane buffer (3 mM MgCl2, 1 mM EDTA, 50 mM Tris HCl pH 7.4) and, in the case of liver samples, glass beads (2.5 mm BioSpec Products). Tissues were stored at −20° C. until analysis.

Reagents and Solutions

Anandamide [ethanolamine-1-3H-] was obtained from American Radiochemicals (specific activity of 60 Ci/mmol). All other reagents were obtained from Sigma-Aldrich. Optiphase Supermix was obtained from Perkin Elmer.

Tissue Preparation

Tissues were thawed on ice; livers were homogenized in a Precellys 24 Dual Tissue Homogenizer (Bertin Technologies) for 2 cycles of 5 sec with an interval of 5 min in ice and brains were homogenized with Heidolph Silent Crusher M (probe 8 F/M) for about 45 sec at maximum velocity. Total protein in homogenates was determined with the BioRad Protein Assay (BioRad) using a standard curve of BSA (50-250 μg/ml).

Enzymatic Assay

Reaction mix (total volume of 200 μl) contained: 2 μM AEA (2 μM AEA+5 nM 3H-AEA), 0.1% fatty acid free BSA, 15 μg (brain) or 1.5 μg (liver) protein, in 1 mM EDTA, 10 mM Tris pH 7.6. After 15 minutes pre-incubation at 37° C. reaction was started by the addition of the substrate solution (cold AEA+radiolabelled AEA+BSA). Reaction was carried out for 7 minutes for liver samples and for 10 min for brain samples and terminated by addition of 400 μL chloroform:methanol (1:1, v/v) solution. Reaction samples were vortex twice, left on ice for 5 minutes and then centrifuged in microfuge (7 minutes, 7000 rpm). Two-hundred μl of supernatants were added to 800 μl Optiphase Supermix scintillation cocktail previously distributed in 24-well plates. Counts per minute (cpm) were determined in a Microbeta TriLux scintillation counter. In each assay blank samples (without protein) were prepared. The percentage of remaining enzymatic activity was calculated in respect to controls and after blank subtraction.

CYPs Metabolic Stability Assay

Stability of the test compounds was performed in MLM (mouse liver microsomes) or HLM (human liver microsomes) in the presence and in the absence of NADPH.

The stability was measured using the incubation mixture (100 µl total volume) contained 1 mg/ml total protein, MgCl$_2$ 5 mM and 50 mM K-phosphate buffer. Samples were incubated in the presence and in the absence of NADPH 1 mM. Reactions were pre-incubated 5 min and the reaction initiated with the compound under test (5 µM for HLM and 50 µM for MLM). Samples were incubated for 60 min in a shaking water bath at 37° C. The reaction was stopped by adding 100 µl of acetonitrile. Samples were then centrifuged, filtered and supernatant injected in HLPC-MSD. Test compounds were dissolved in DMSO and the final concentration of DMSO in the reaction was below 0.5% (v/v). At T0 acetonitrile was added before adding the compound. All experiments were performed with samples in duplicate.

Compounds Tested:

Compound 1=(N-methyl-4-(3-(sulfamoylamino)phenyl)-N-(tetrahydro-2H-pyran-4-yl)-1H-imidazole-1-carboxamide).

Compound 2=((4-(4-Hydroxy-3-methylphenyl)-N-methyl-N-(1-propionylpiperidin-4-yl)-1H-imidazole-1-carboxamide).

Compound 3=((N-(1-(Cyclopropanecarbonyl)piperidin-4-yl)-4-(4-hydroxy-3-methylphenyl)-N-methyl-1H-imidazole-1-carboxamide).

|  | FAAH Activity (%)<br>Br · h · 3 mg/kg · 8 h · po | FAAH Activity (%)<br>Lv · h · 3 mg/kg · 8 h · po |
| --- | --- | --- |
| Compound 1 | 117 | 4.9 |
| Compound 2 | 81.7 | 1.5 |
| Compound 3 | 91.7 | 1.8 |

As can be seen from the above table, compounds 1, 2 and 3 are all relatively potent compounds in terms of FAAH inhibition in the liver.

Peripheral selectivity can be calculated by dividing the FAAH activity in the liver by the FAAH activity in the brain. When doing this, a lower number shows a compound is peripherally more selective. The results are given in the table below:

|  | Peripheral Selectivity |
| --- | --- |
| Compound 1 | 0.042 |
| Compound 2 | 0.018 |
| Compound 3 | 0.020 |

These results show that compounds 2 and 3 are the most peripherally selective compounds but that all the compounds show relatively high peripheral selectivity.

Additional data relating to the activity of FAAH at various concentrations for the compounds are given in the table below:

| | FAAH Activity (%) mouse Liver | | | | | |
| --- | --- | --- | --- | --- | --- | --- |
| | 1 h | | 8 h | | | |
| | 1 mg/kg | 0.1 mg/kg | 0.3 mg/kg | 0.1 mg/kg | 0.03 mg/kg | 0.01 mg/kg |
| Compound 1 | 8.5 | | 36.1 | | | |
| Compound 2 | 2.3 | 21.9 | 5.6 | 6.7 | 42.9 | 48.2 |
| Compound 3 | | 37.9 | 7.2 | 10.7 | 53.0 | 56.3 |

As can be seen above, compounds 2 and 3 are the most potent as they inhibit FAAH activity even at a relatively low dose. However, all the compounds are relatively potent.

Further, similar experiments were conducted in rats which gave the following results:

| | FAAH Activity (%) rat Liver | | | | |
| --- | --- | --- | --- | --- | --- |
| | Dose: 0.1 mg/kg | | Dose: 1 mg/k9 | | |
| | 1 h | 8 h | 1 h | 8 h | 24 h |
| Compound 1 | | | 9.8 | 4.8 | 22.7 |
| Compound 2 | 78.2 | 59.1 | 25.7 | 18.2 | 17.8 |
| Compound 3 | 83.5 | 62.5 | | | |

As can be seen above, all the compounds show relatively good inhibition in rat liver and are relatively potent.

Metabolic Stability

The below table shows the metabolic stability of the compounds. The stability data are given as % of remaining compound after 1 h exposure to MLM or HLM. 100% means no metabolic reaction at all and 0% corresponds to full enzymatic degradation. "CYP−" refers to the absence of cofactor (NADPH) which is essential for CYP metabolic reactions. Therefore "CYP−" can be regarded as control value. "CYP+" refers to the presence of cofactor and the enzymatic degradation may take place according to the stability of the test compound. As can be seen, all the compounds are metabolically stable.

| | Metabolic Stability (% of Remaining) | | | |
| --- | --- | --- | --- | --- |
| | Mouse | | Human | |
| | CYP+ | CYP− | CYP+ | CYP− |
| Compound 1 | 93 | 100 | 96 | 102 |
| Compound 2 | 86 | 83 | 100 | 94 |
| Compound 3 | 98 | 91 | 99 | 102 |

The invention claimed is:

1. A compound having a structure selected from the group consisting of:

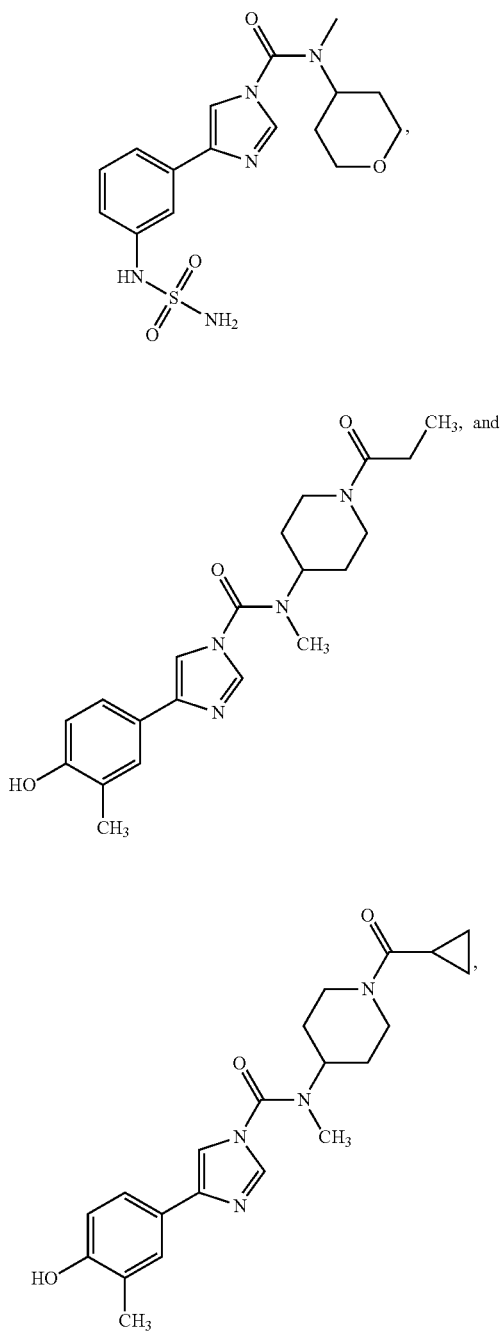 [SMILES: CN(C(=O)n1cnc(-c2cccc(NS(N)(=O)=O)c2)c1)C1CCOCC1 ; CCC(=O)N1CCC(N(C)C(=O)n2cnc(-c3ccc(O)c(C)c3)c2)CC1 ; Cc1cc(-c2cn(C(=O)N(C)C3CCN(C(=O)C4CC4)CC3)cn2)ccc1O]

or a pharmaceutically acceptable salt thereof.

2. The compound of claim 1, wherein the pharmaceutically acceptable salt is selected from the group consisting of a hydrochloride salt, acetate salt, trifluoroacetate salt, methanesulfonate salt, 2-hydroxypropane-1,2,2-tricarboxylate salt, (2R,3R)-2,3-dihydroxysuccinate salt, phosphate salt, sulphate salt, benzoate salt, 2-hydroxy-benzoate salt, S-(+)-mandelate salt, S-(−)-malate salt, S-(−) pyroglutamate salt, pyruvate salt, p-toluenesulfonate salt, 1-R-(−)-camphorsulfonate salt, fumarate salt, maleate salt and oxalate salt.

3. The compound of claim 1 or the pharmaceutically acceptable salt thereof, wherein the compound has the structure 4. The compound of claim 1 or the pharmaceutically acceptable salt thereof, wherein the compound has the structure

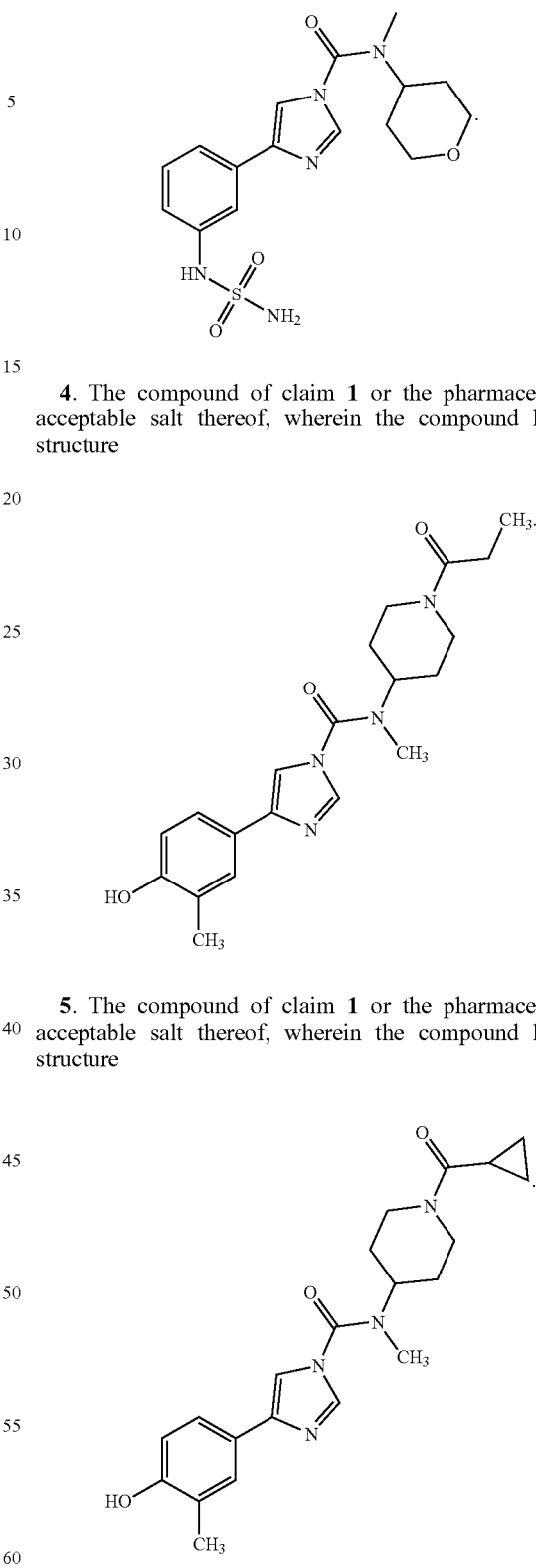

5. The compound of claim 1 or the pharmaceutically acceptable salt thereof, wherein the compound has the structure 6. A pharmaceutical composition comprising a compound according to claim 1, together with one or more pharmaceutically acceptable excipients.

7. The pharmaceutical composition of claim 6, further comprising one or more additional active pharmaceutical ingredients.

8. The pharmaceutical composition of claim 6, wherein the composition is formulated for oral administration.

9. The pharmaceutical composition of claim 6, wherein the composition is in the form of a sterile injectable preparation.

10. The pharmaceutical composition of claim 7, wherein the one or more additional active pharmaceutical ingredients are selected from the group consisting of anandamide, oleoyl ethanolamide, and palmitoyl ethanolamide.

11. A method of treatment of an eye condition selected from the group consisting of ocular hypertension and glaucoma, the method comprising the administration, to a subject in need of such treatment, of a therapeutically effective amount of a compound according to claim 1.

12. The method of claim 11, wherein the method comprises further administration of one or more additional active pharmaceutical ingredients, wherein the compound is administered simultaneously with or staggered with respect to, the one or more additional active pharmaceutical ingredients.

13. The method of claim 12, wherein the one or more additional active pharmaceutical ingredients are selected from the group consisting of anandamide, oleoyl ethanolamide and palmitoyl ethanolamide.

14. The method of claim 11, wherein the eye condition is ocular hypertension.

15. The method of claim 11, wherein the eye condition is glaucoma.

* * * * *